United States Patent

Yanagidaira et al.

[11] Patent Number: 5,954,629
[45] Date of Patent: *Sep. 21, 1999

[54] BRAIN WAVE INDUCING SYSTEM

[75] Inventors: Masatoshi Yanagidaira; Yuichi Kimikawa; Takeshi Fukami; Mitsuo Yasushi, all of Saitama-ken, Japan

[73] Assignee: Pioneer Electronic Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/797,655

[22] Filed: Jan. 31, 1997

[30] Foreign Application Priority Data

Feb. 21, 1996 [JP] Japan .................................. 8-033848

[51] Int. Cl.⁶ .................................................. A61M 21/00
[52] U.S. Cl. ................................. 600/27; 600/26; 600/28
[58] Field of Search ............................... 600/26–28, 544, 600/545, 558; 128/731, 732, 745

[56] References Cited

U.S. PATENT DOCUMENTS

| | | | |
|---|---|---|---|
| 5,241,967 | 9/1993 | Yasushi et al. | 600/27 |
| 5,495,853 | 3/1996 | Yasushi | 600/27 |
| 5,613,498 | 3/1997 | Yasushi et al. | 600/27 |

*Primary Examiner*—Linda C. M. Dvorak
*Assistant Examiner*—Rosiland Kearney
*Attorney, Agent, or Firm*—Nikaido, Marmelstein, Murray & Oram LLP

[57] ABSTRACT

Sensors are provided for detecting brain waves of a user, and a band-pass filter is provided for extracting a particular brain waves including an α wave included in a detected brain wave. The band-pass filter comprises a first band-pass filter having a narrow pass band, and a second band-pass filter having a wide pass band. One of the first and second band-pass filters is selected, and a stimulation signal is produced in dependency on an α wave extracted by a selected band-pass filter. In accordance with the stimulation signal, a stimulation light is emitted to the user in order to induce the user to relax or sleeping state.

6 Claims, 12 Drawing Sheets

BRAIN WAVE INDUCING SYSTEM

BACKGROUND OF THE INVENTION

The present invention relates to a system for inducing a brain wave of the person, and more particularly to a system for providing a relaxation effect and an activation effect in a state of mind of the person.

In the system, the brain wave of the person is induced by a feedback control including a brain of the person. Namely, the brain wave of the person is detected, and a specific element of the brain wave, such as an α wave is extracted. By using the extracted brain wave, a signal for controlling stimulation by light is produced for inducing a desired brain wave. The stimulating light is applied to the person for stimulating the brain, thereby inducing the desired brain wave. Thus, the desired brain wave can tie powerfully and quickly induced by an induction effect of the feedback control.

Such a system is used for as a sole system, or as a combination system with an audio healing system or a massage device.

FIG. 13 shows a conventional brain wave inducing system employed with a feedback loop structure including a brain of a user. The system comprises a sensor unit 10 for detecting a brain wave of the user, a light signal producing system 20 for extracting a specific element of the brain wave and producing a light stimulation signal, and an actuating unit 30 for applying the stimulating light based on the light stimulation signal to the user.

The sensor unit 10 comprises a headband 11 to be easily put on or removed from a head of the user, and an ear clip 14a detachably clipped on an ear of the user. A pair of electrodes 12 and 13 as brain wave sensors are provided on an inner portion of the headband 11 so that the electrodes are touched on a forehead of the user when the headband 11 is put on the head. The ear clip 14a has an electrode 14 as a brain wave sensor to be touched on the ear.

The actuating unit 30 comprises a capsule or cover 31 to cover the head and face of the user, and a light emitting member 32 provided on an inner portion of the the cover 31 at a position such that the stimulation light is applied to eyes of the user.

The light signal producing system 20 is provided for extracting the specific element of the brain wave and producing a light stimulation signal for controlling stimulation by light based on the extracted brain wave, thereby inducing the desired brain wave. The system comprises a biological amplifier 24 to which outputs of the electrodes 12, 13 and 14 of the sensor unit 10 are connected, an A/D converter 25, an automatic gain control circuit (AGC) 26, a band-pass filter (BPF) 27, a D/A converter 28, and an amplifier 29 connected to the light emitting member 32 of the actuating unit 30.

The electrodes 12 of the sensor unit 10 is connected to a GND input of the amplifier 24, the electrode 13 is connected to a minus input, and the electrode 14 is connected to a plus input, respectively. The amplifier 24 amplifies a very weak brain wave signal detected by the sensor unit 10 to a predetermined value. The amplified brain wave signal is applied to the A/D converter 25 for converting the signal into a digital signal of 8 bits, for example. The digital brain wave signal is applied to the AGC 26 in which the gain of the signal is adjusted for a following stage. The BPF 27 operates to extract a predetermined element of the band of the brain wave signal. The D/A converter 28 converts the extracted band element of the brain wave of the digital signal into an analog signal. The amplifier 30 amplifies the analog signal so as to control the light emitted from the light emitting member 32 of the actuating unit 30.

The light signal producing system 20 further comprises a microprocessor unit (MPU) 22 having a controller 23. The AGC 26 and BPF 27 are operated by programs of the MPU 22. A remote controller 21 is provided for applying external operating commands to the controller 23. The controller 23 controls tasks and other circuits in the system in accordance with the operations of the remote controller 21. For example, the controller 23 produces a message A to initialize the BPF 27, and controls the amplifier 29 of gain variable for adjusting the amount of the stimulation light in accordance with a choice of the user.

In the BPF 27, since the α wave of the brain wave is effective to provide a relaxation effect, a predetermined band is set based on the α wave. The α wave is a basic wave appeared in large amounts when an awakening normal adult rests, and has a feature that the dispersion thereof is small when the person is relaxed in a clearer awakening state. Thus, the BPF 27 has a frequency characteristic of Q=10 (Q=(center frequency f)/(band width the gain of which becomes lower than the gain of the center frequency f by 3 dB)). The α wave has a waveform having an amplitude between 10 to 100 μV and frequency between 8 to 14 Hz. However, there is an individual difference in α wave characteristics. Thus, the center frequency of the BPF 27 is set to be varied for covering the range of the frequency.

Furthermore, in the BPF 27, since a proper α wave is determined in dependency on the person, influence caused by the individual difference is controlled to be absorbed. If a person having a high frequency of α wave is induced to a range of a low frequency of α wave, the person may feel bad because of a large difference between the frequencies. In order to solve the problem, at initialization, the BPF 27 operates to change the center frequency step by step to sweep the band of the α wave. Then, an average frequency of the brain wave signal is calculated to set the center frequency to a value lower than the average value by 0.5 Hz. Thereafter, the center frequency is fixed to the set value during the procedure. Thus, an inconvenience such as a bad feeling is avoided.

Describing the operation of the system, the brain wave of the user is detected by the sensor unit 10. The detected brain wave is amplified by the amplifier 24. The amplified brain wave is applied through the A/D converter 25 and the AGC 26 to the BPF 27 where a proper α wave is extracted. The extracted brain wave is applied to the amplifier 29 through the D/A converter 28. The amplifier 29 produces an electric signal for light stimulation based on the extracted brain wave. The light stimulating signal is applied to the actuating unit 30. The light emitting member 32 emits the light for stimulation which is applied to the closed eyes of the user, thereby stimulating the brain.

Thus, the user is sufficiently applied with a proper light stimulation produced based on own α wave to be induced to a relaxed state in a short time.

As hereinbefore described, a main purpose of the conventional brain wave inducing system is to induce the person to a relaxed condition.

However, if the system is provided with not only the relaxation effect but also a sleep inducing effect for positively inducing the person to sleep, the product worth of the system may be increased. In the improvement, economically, it is necessary to lower developing and manufacturing costs as less as possible.

In order to realize the brain wave inducing system provided with the sleep inducing effect in addition to the relaxation effect by using the basic composition of the conventional system with small change, technical means must be designed for the system.

Furthermore, in the conventional system, one of the brain wave sensors is mounted on the head of the user for detecting the brain wave. However, the condition that the sensor is directly mounted on a part of the body may cause the user to be nervous. In such a case, a sufficient sleep inducing effect can not be obtained. If the system is used during sleeping, the system may interfere natural moving such as turning in sleep.

Therefore, it is preferable that the system can be used without mounting sensors on the body.

Furthermore, the ear clip is used as the other brain sensor because the ear is near the brain, and has no muscles. Consequently, noises to be caused by action of the muscle do not produce. In addition, the electrode can be easily attached to the ear by the ear clip.

However, the ear clip stimulates the ear compared with the headband, and may hurt the ear if it is used for a long time.

Therefore, it is desirable that even if the user must mount the sensor on the body, the relaxation and sleep inducing effects, or at least the relaxation effect can be easily obtained.

SUMMARY OF THE INVENTION

An object of the present invention is to provide a brain wave inducing system which may have relaxation inducing effect and sleep inducing effect.

Another object of the present invention is to provide a system with which relaxation effect and sleep inducing effect are easily obtained.

According to the present invention, there is provided a brain wave inducing system comprising sensors for detecting brain waves of a user, a band-pass filter for extracting a particular brain waves including an $\alpha$ wave included in a detected brain wave, the band-pass filter comprising a first band-pass filter having a narrow pass band, and a second band-pass filter having a wide pass band, first selecting means for selecting one of the first and second band-pass filters, output means for producing a stimulation signal dependent on an $\alpha$ wave extracted by a selected band-pass filter, and light emitting means responsive to the stimulation signal for emitting a stimulation light to the user.

A memory is provided for recording the extracted brain waves and for reproducing the recorded brain waves, and second selecting means for selecting either of the recording or reproducing of the brain waves.

The sensors are mounted on an eye mask to be attached to a forehead of the user.

The detecting means is provided for detecting a sleep falling point when the user falls into sleep. The detecting means detects the sleep falling point by detecting a time when $\alpha$ wave appearance rate reduces 50% from a reference value.

These and other objects and features of the present invention will become more apparent from the following detailed description with reference to the accompanying drawings.

DETAILED DESCRIPTION OF THE PREFERRED EMBODIMENTS (First embodiment)

Figure 1:
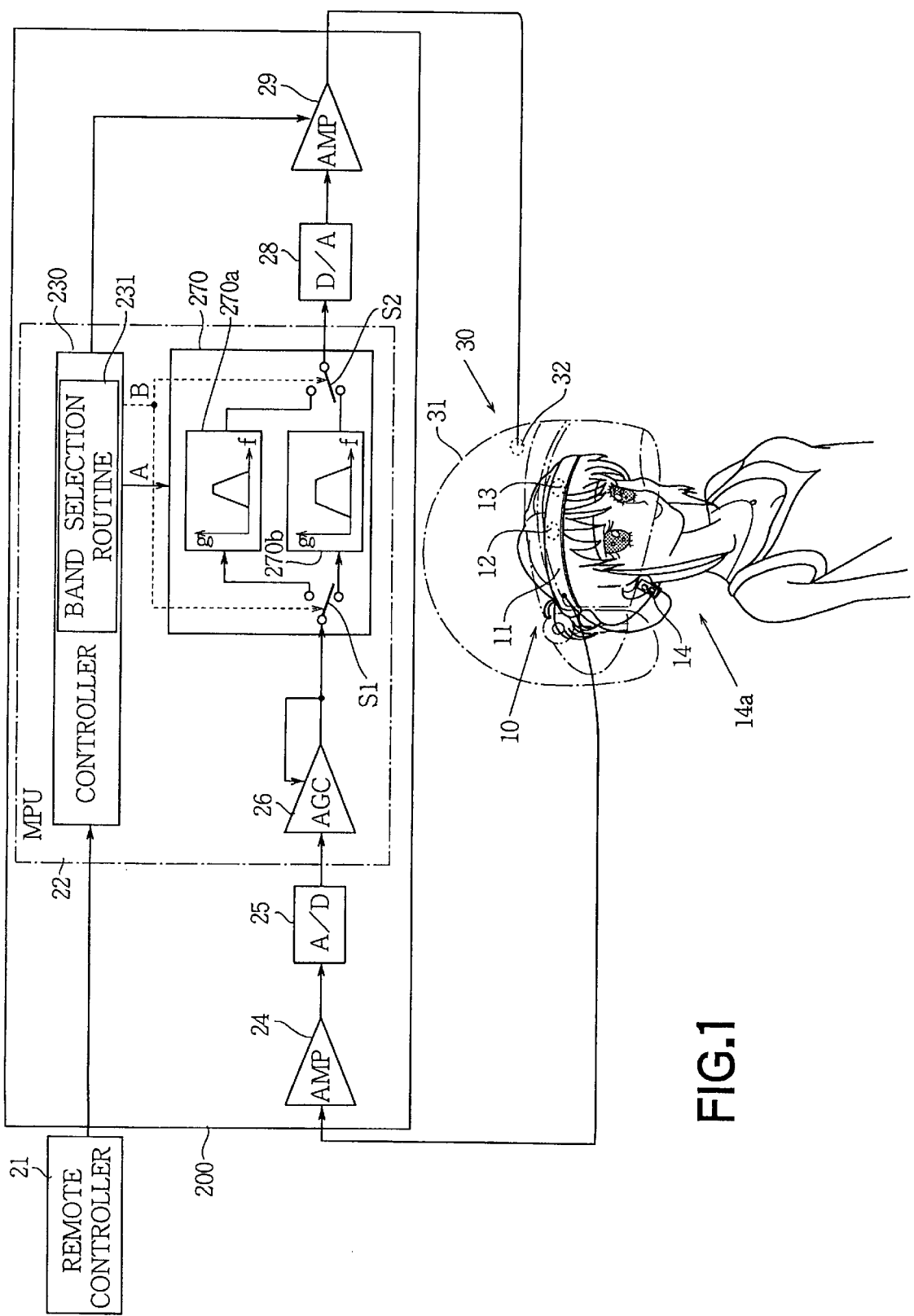
FIG. 1 is a diagram showing a mind-refresh system to which a brain wave inducing system according to the present invention is applied.

FIG. 1 shows a brain wave inducing system of the present invention applied to a mind refresh system.

Figure 2:
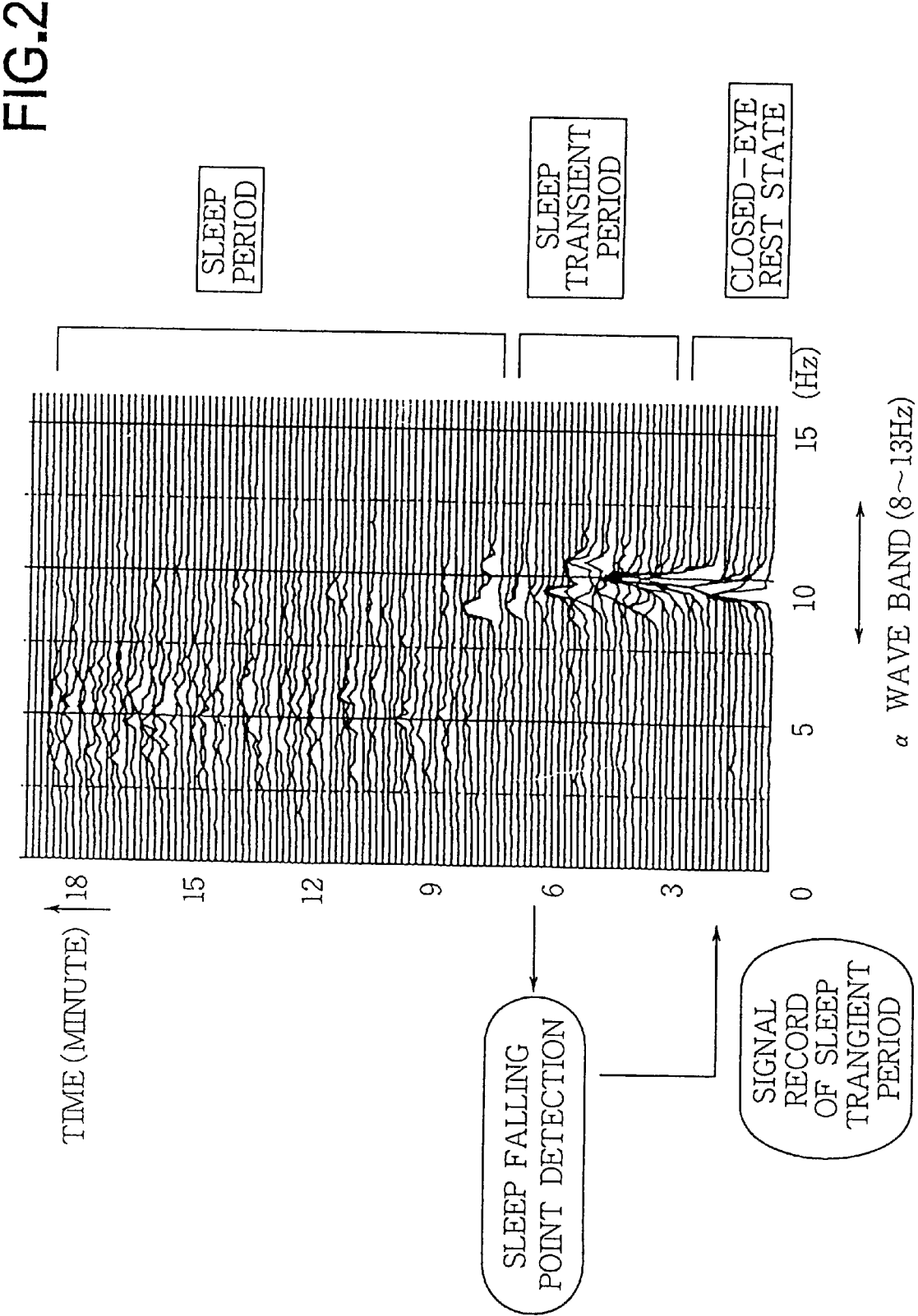
FIG. 2 is a diagram showing a frequency characteristic of the brain wave when a person drops off to sleep.

It is known that when the person closes the eyes, the brain wave produces the $\alpha$ wave, and when the person drops off to sleep, the $\alpha$ wave changes to a 73 wave a frequency of which is lower than the $\alpha$ wave. FIG. 2 shows frequency characteristics of the brain wave until the person falls into sleep. It will be seen that there are states where the person closes eyes and rests for 3 minutes, and falls into sleep through a sleep transient period for 7 minutes. The state of mind of the person changes from a relaxation state in the closed-eyes rest period, a special doze state where a flash of an idea or an image may be easily produced, and to a sleep state. The $\alpha$ wave has a small dispersion in the closed-eye rest period, and is repeatedly disappeared and reappeared with fluctuation in the sleep transient period, and changes to the e wave in the sleep period. The attention of the person is gradually reduced to reduce the awakening level.

Figure 13:
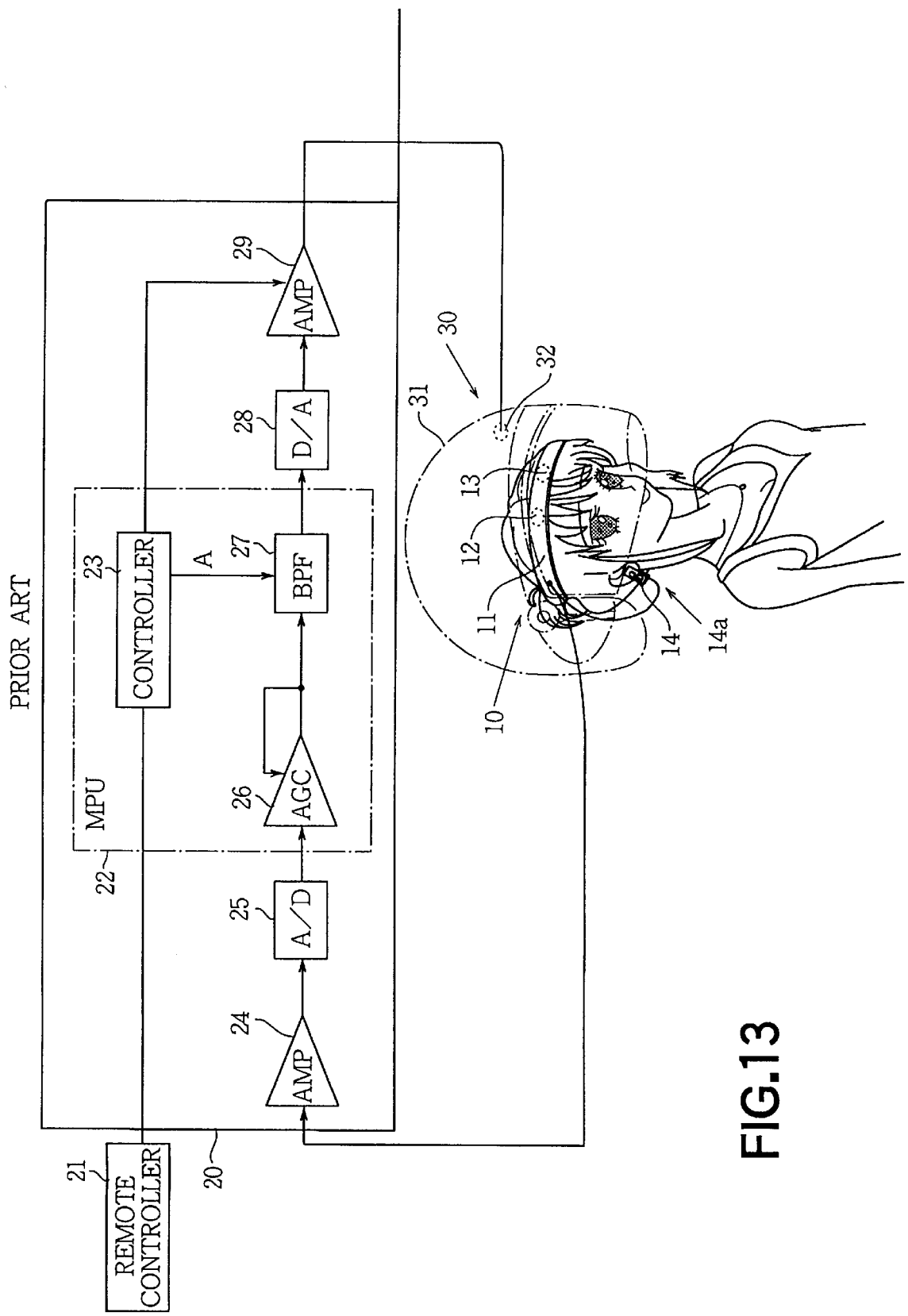
FIG. 13 is a diagram showing a conventional brain wave inducing system.

Referring back to FIG. 1, in the brain wave inducing system, structures which are the same as those of the conventional system of FIG. 13 are identified with the same reference numerals as FIG. 13, and descriptions thereof are omitted.

A light signal producing system 200 has a BPF unit 270 comprising a first BPF 270a and a second BPF 270b, and switches S1 and S2 for selectively connecting the first BPF 270a and the second BPF 270b to the AGC 26 and the D/A converter 28. The first BPF 270a has (Q=10 with a narrow pass band corresponding to the $\alpha$ wave in the eye-closed rest state. The second BPF 270b has Q=5 with a wide pass band corresponding to support frequency ranges of fluctuation of the $\alpha$ wave in the sleep transient state. The center frequency and the Q of each of the first and second BPFs are provided to be changeable.

A controller 230 of the MPU 22 has a band selection routine 231 having a normal mode and a sleep induction mode. One of the modes is selected by operating a remote controller 121, and the band selection routine 231 produces a flag B which is applied to the BPF unit 270 for selectively operating the switches S1 and S2 to close contacts for the first BPF 270a or the second BPF 270b. Thus, the α wave is extracted from a proper BPF in accordance with the selected mode.

In operation, the brain wave of the user is detected by the sensor unit 10. The detected brain wave is amplified by the amplifier 24. The amplified brain wave is applied through the A/D converter 25 and the AGC 26 to the BPF 270 where a proper α wave is extracted. Namely, when the normal mode is selected by the remote controller 121, the flag B of the normal mode is applied to the switches S1 and S2 of the BPF unit 270 which are operated to close the first BPF 270a. Thus, the output signal of the AGC 26 is applied to the first BPF 270a through the switch S1. The first BPF 270a extracts the α wave in the eye-closed rest state which is applied to the D/A converter 28 through the switch S2. Thus, a stimulation signal having a frequency corresponding to the extracted α wave is produced. The stimulation signal is applied to the light emitting member 32 through the amplifier 29. The light emitting member 32 flickers at the frequency of the stimulation signal. Thus, the α wave in the eye-closed rest state is applied by the feedback control, thereby obtaining the relaxation effect.

When the sleep induction mode is selected, the flag B of the sleep induction mode is applied to the switches S1 and S2 which are operated to close the second BPF 270b. Thus, the output signal of the AGC 26 is applied to the second BPF 270b through the switch S1. The second BPF 270b extracts the α wave in the sleep transient state which is applied to the D/A converter 28 through the switch S2. Thus, even if the α wave is fluctuated in the sleep transient state, approximately all of the α wave is applied by the feedback control, thereby obtaining the sleep inducing effect.

From the foregoing, the feedback control is repeated so that the induction operation of brain wave for increasing the sleep inducing effect is provided in addition to the induction operation for increasing the relaxation effect. A desired effect can be automatically obtained by selecting a desired mode in dependency on a body condition of the user.

(Second embodiment)

Figure 3:
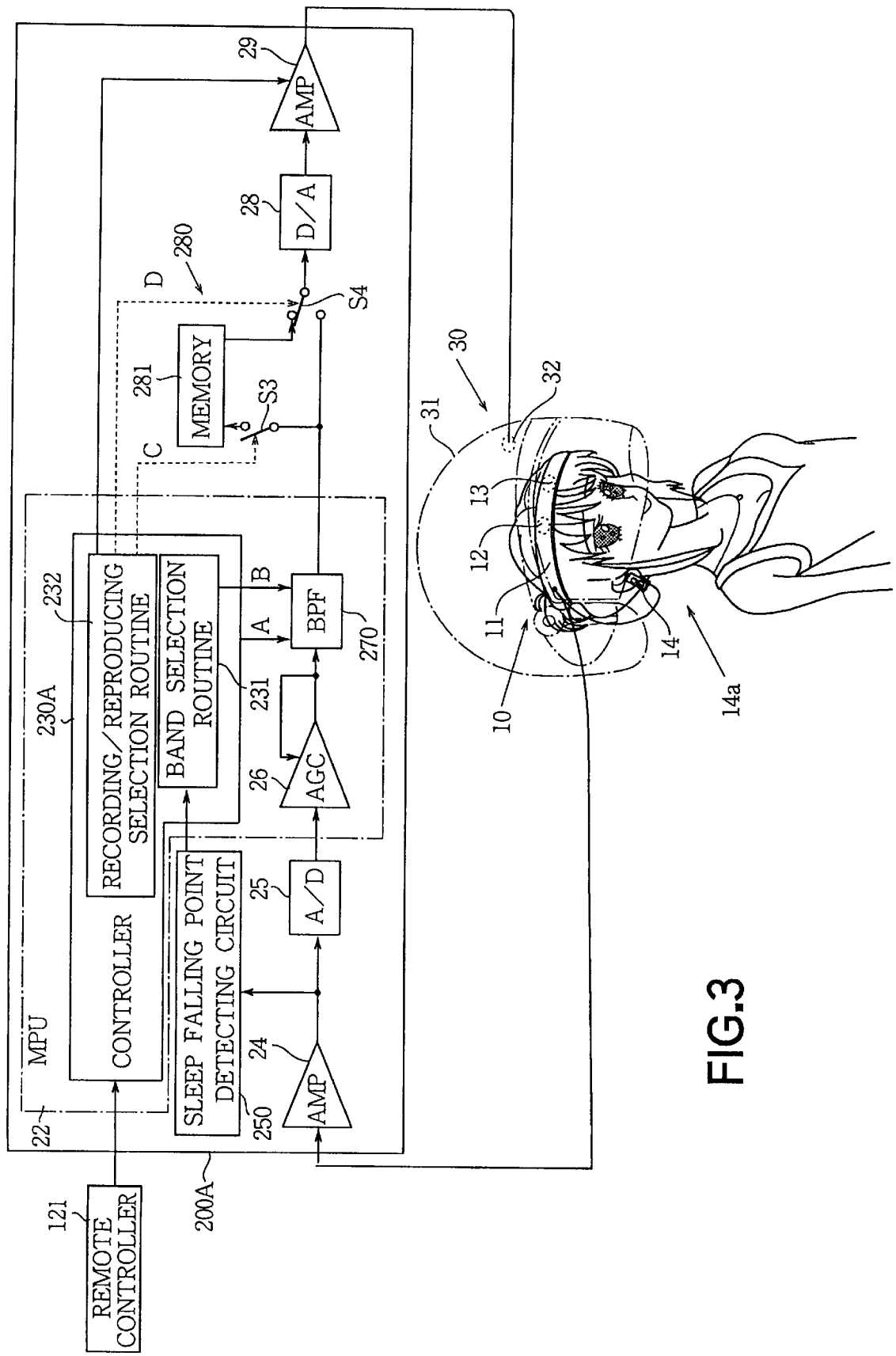
FIG. 3 is a diagram showing a second embodiment of the brain wave inducing system of the present invention.

Referring to FIG. 3 showing a second embodiment of the present invention, the system is provided with a recording/reproducing function for a proper retracted brain wave when the person drops off to sleep. In a light signal producing system 200A, a controller 230A of the MPU 22 further has a recording/reproducing selection routine 232. Furthermore, a sleep falling point detecting circuit 250 and a recording/reproducing changeover circuit 280 are provided.

Other parts are the same as those of the first embodiment of FIG. 1 and identified with the same reference numerals as FIG. 1.

The recording/reproducing changeover circuit 280 comprises a memory 281 such as a ring buffer provided between the BPF unit 270 and the D/A converter 28 for storing the brain wave extracted by the BPF unit 270, and for applying the stored data of the brain wave to the D/A converter 28. The memory 281 has a storage capacity for storing data of the extracted brain wave for the BPF unit 270 for a few minutes.

The recording/reproducing changeover circuit 280 further has an input switching circuit S3 for connecting the BPF unit 270 to the memory 281, and an output switching circuit S4 for selectively connecting the BPF unit 270 and the memory 281 to the D/A converter 28.

The recording/reproducing selection routine 232 has a recording mode for recording the output of the BPF unit 270 in the memory 281, and a reproducing mode for reproducing the data stored in the memory 281. Each mode is selected by operating the remote controller 121, and the recording/reproducing selection routine 232 produces control signals C and D which are applied to the switching circuits S3 and S4, respectively.

When the recording mode is selected, the control signal C operates the switching circuit S3 to close it. The control signal D operates the switching circuit S4 to connect the BPF unit 270 to the D/A converter 28. Thus, the extracted brain wave of the BPF unit 270 is applied to the memory 281 and stored therein, and to the D/A converter 28.

On the other hand, when the reproducing mode is selected, the control signal C operates the switching circuit S3 to open it. The control signal D operates the switching circuit S4 to connect the memory 281 to the D/A converter 28. Thus, the brain wave data stored in the memory 281 is reproduced and applied to the D/A converter 28.

The sleep falling point detecting circuit 250 is provided for detecting a sleep falling point in accordance with the α wave. The sleep falling point detecting circuit 250 is applied with the brain wave signal from the amplifier 24 and detects that the amount of the α wave included in the brain wave reduces compared with the amount of the α wave in the closed-eye rest state. Thus, the sleep falling point in which the person falls into sleep through the sleep trasient period is detected. The detected signal is applied to the controller 230A of the MPU 22.

The detecting operation of the sleep falling point detecting circuit 250 will be described in detail. First, an appearance rate of the α wave is calculated by (accumulated time of a frequent region of the α wave/1 minute)×100%. A reference value of the α wave appearance rate is obtained based on an average of the α wave appearance rate from a start point. When the α wave appearance rate is less than 50% of the reference value, it is determined that the point at that time is the sleep falling point. In an example shown in FIG. 4b, when 4 minutes have passed, the sleep falling point is detected. In order to prevent erroneous detection caused by noises made by opening and closing eyes, and muscles, the averaging process is used.

Figure 4:
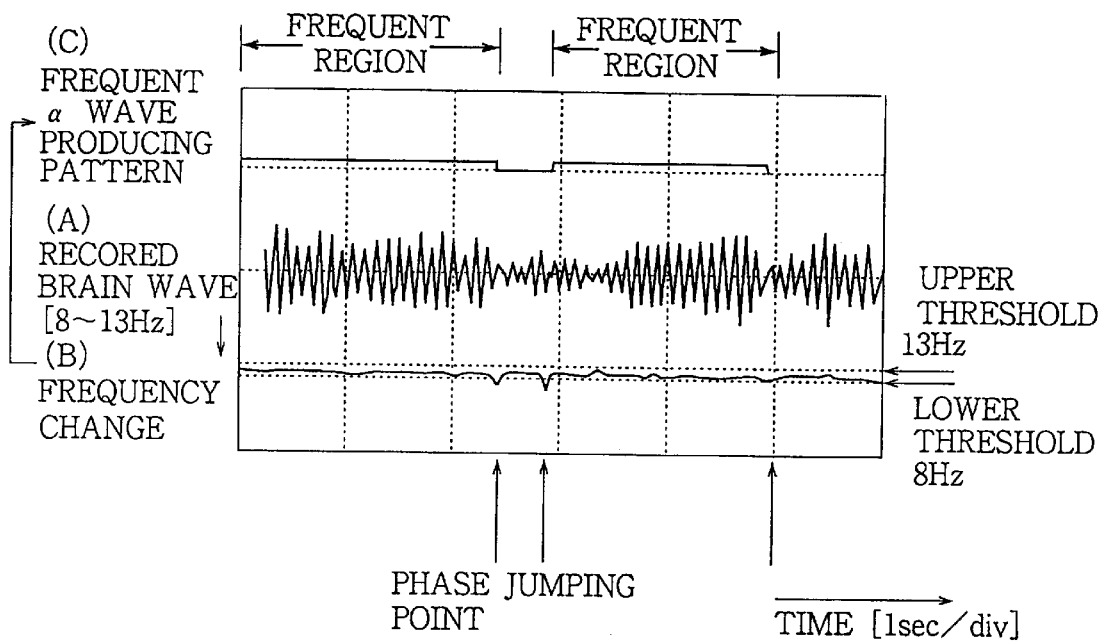
FIGS. 4a and 4b are diagrams showing characteristics of the brain wave when the person sleeps.
Figure 4:
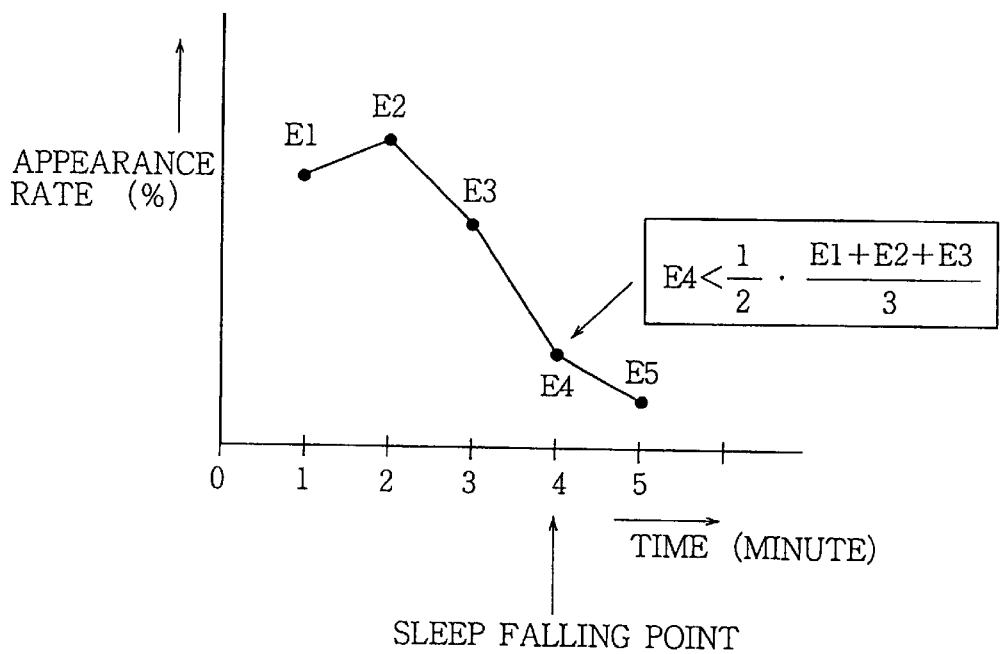

In order to obtain the frequent region of the α wave, the frequency of the detected brain wave is calculated as shown in FIG. 4a. When the frequency is deflected from the range between 8 and 13 Hz, a jumping point of phase is determined. When a period of the phase jumping point exceeds 1 second, that period is determined as the frequent producing region of the α wave. An instantaneous frequency of the detected brain wave is obtained by a known complexed Demodulation (CD) method.

As a result of experiments based on a sincipital brain wave, the sleep falling point was detected at high probability, more than 80%.

When the controller 230A of the MPU 22 is applied with the sleep falling point signal from the sleep falling point detecting circuit 250, the recording/reproducing selection routine 232 operates the control signal C to open the switching circuit S3. Thus, the data recording of the BPF unit 270 in the memory 281 is stopped, and the stored content is fixed corresponding to the sleep falling point detection.

Describing the operation of the system, when the user selects the recording mode, the brain wave signal of the BPF unit 270 is applied to the D/A converter 28 through the switching circuit S4. Thus, the relaxation effect and the sleep inducing effect are selectively obtained.

At the same time, the brain wave signal of the BPF unit 270 is applied to the memory 281 through the switching circuit S3 and stored therein.

When the user falls into sleep, and the sleep falling point detecting circuit 250 detects the sleep falling point, the switching circuit S3 is operated to be opened. Thus, the content of the memory 281 is fixed at the time. The brain wave signal before the sleep falling point is maintained within an allowable range of the storage capacity of the memory.

At the subsequent utilization of the system, if the reproducing mode is selected by the user, the brain wave data stored in the memory 281 is reproduced and applied to the D/A converter 28. In the reproducing mode, since the light signal is produced in accordance with the content of the memory, it is not necessary to use the sensor unit 10. The inducing effect is sufficiently obtained without the brain wave sensor.

In the reproducing mode, the amplification factor is gradually reduced to fade out the light stimulation because the light stimulation disturbs the sleep of the user. Thus, luminance is reduced.

It is effective to change luminance in dependency on the appearance of the α wave and the result of the sleep falling point detection, and to changeover the output of the BPF unit 270.

(Third embodiment)

Figure 5:
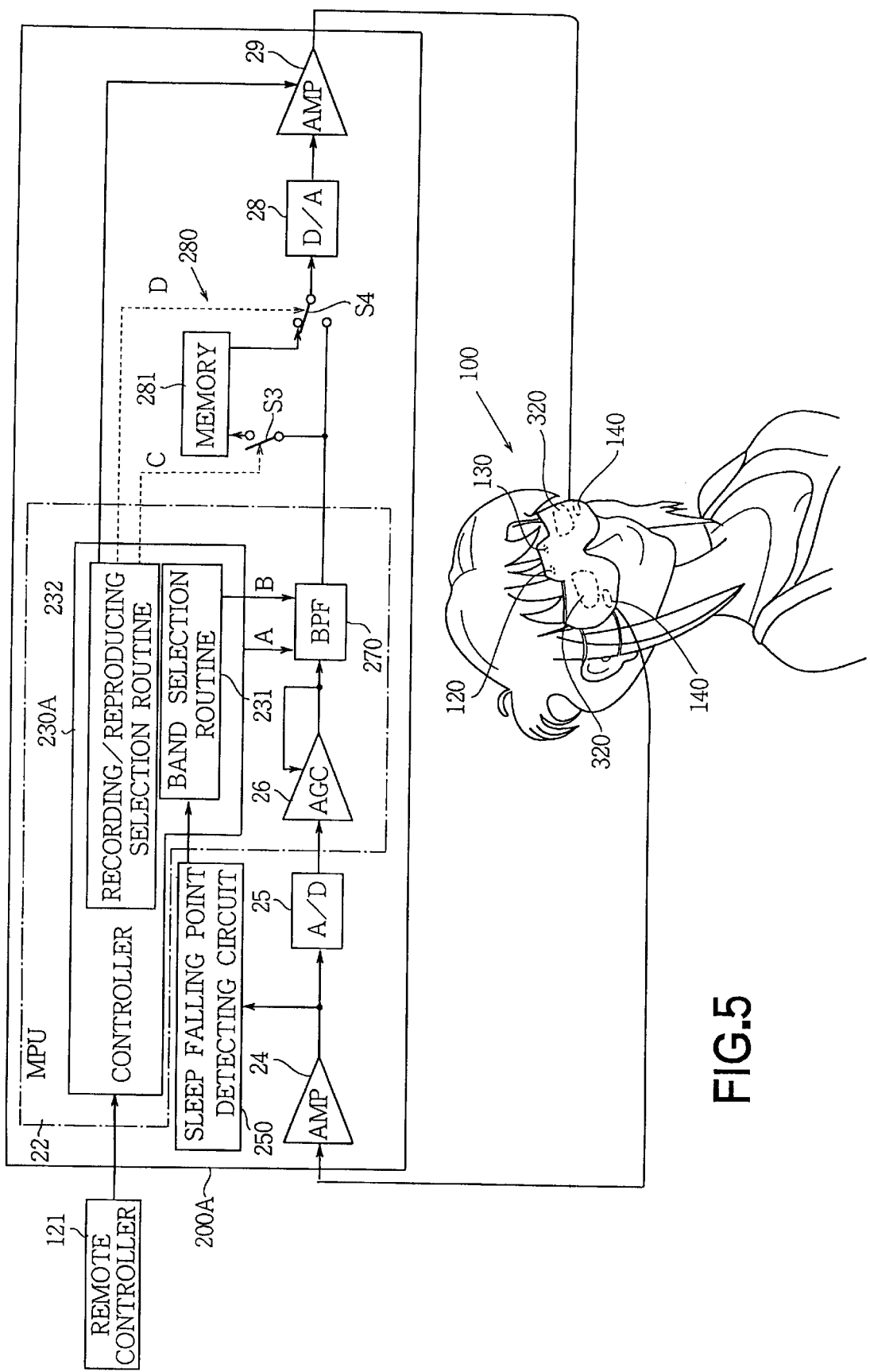
FIG. 5 is a diagram showing a third embodiment of the present invention.

Referring to FIG. 5 showing a third embodiment of the present invention, the system has a face mounted device 100 in the form of an eye mask in place of the sensor unit and the actuating unit of the previous embodiments, and the light signal producing system 200A which is the same as the second embodiment of FIG. 3.

Figure 6:
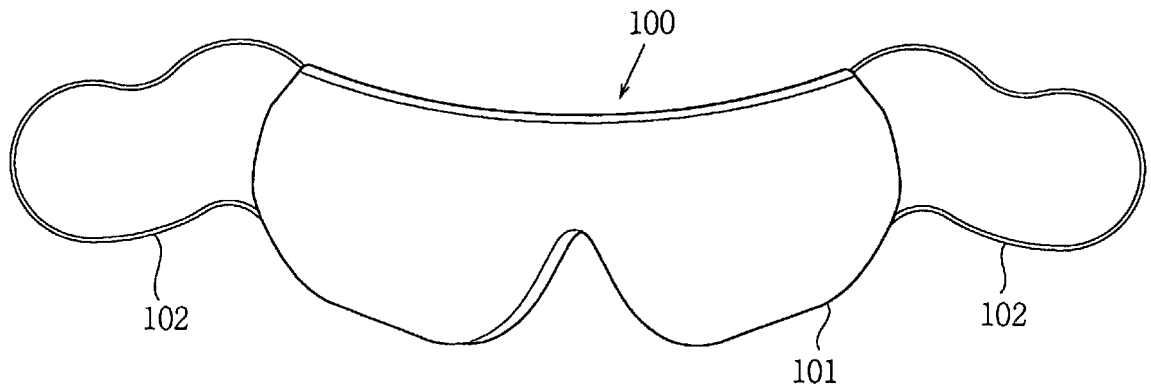
FIGS. 6a to 6c are schematic diagrams showing an eye mask.
Figure 6:
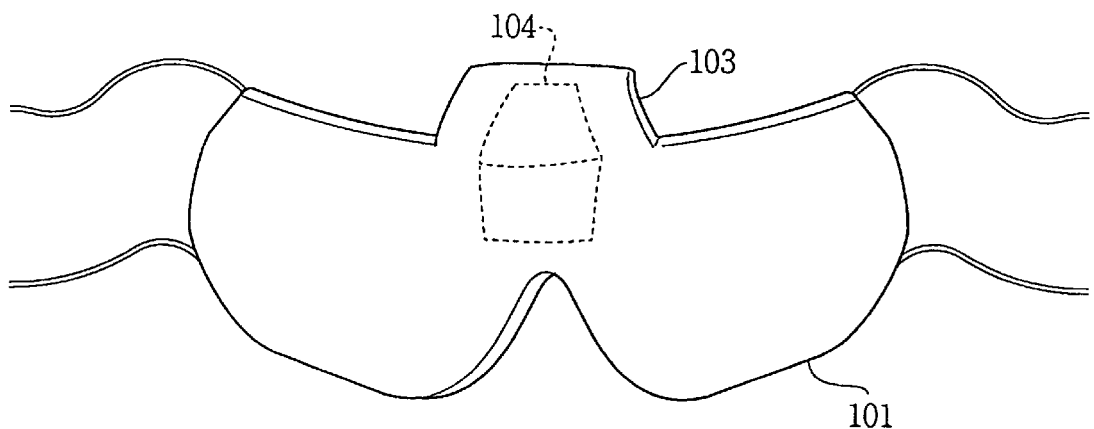
Figure 6:
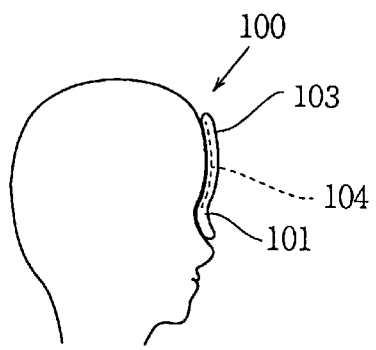

Referring to FIG. 6a, the eye mask device 100 has a bandage 101 for shielding the eyes of the user and a pair of ear straps 102 made of rubber secured to the both sides of the bandage 101.

As shown in FIG. 6b, a lug is sewed on an upper portion of the bandage 101 to form a forehead portion 103 which is abutted on a forehead of the user when the eye mask device 100 is put on the face. In the forehead portion 103, a reinforcement member 104 of a resilient plate is embedded so as to be curved along the forehead. Thus, when the eye mask device 100 is put on the face of the user as shown in FIG. 6c, the forehead portion 103 is securely abutted on the forehead.

Figure 7:
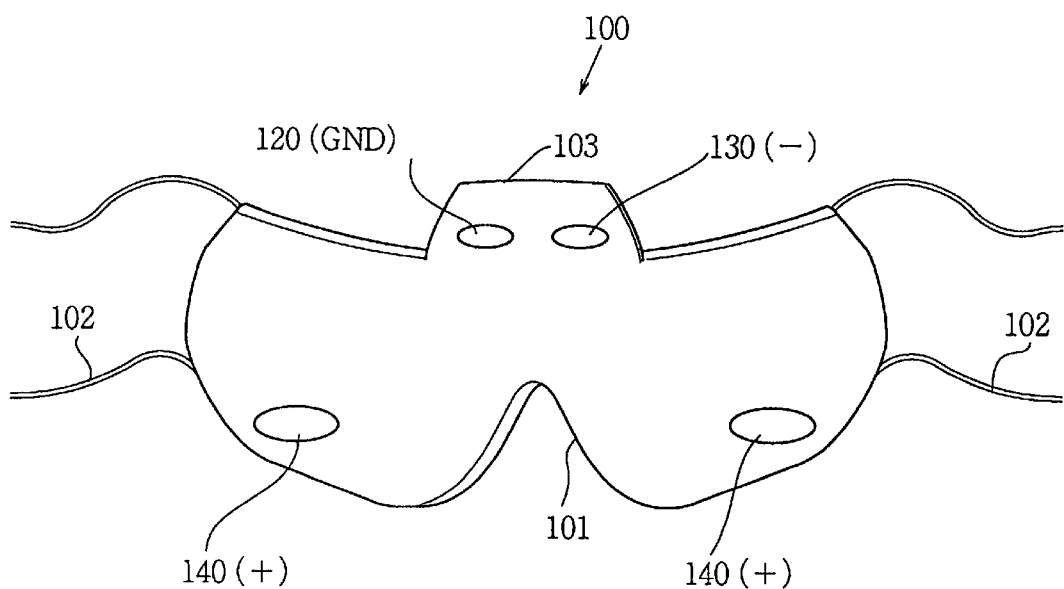
FIGS. 7a and 7b are schematic diagrams showing the eye mask.
Figure 7:
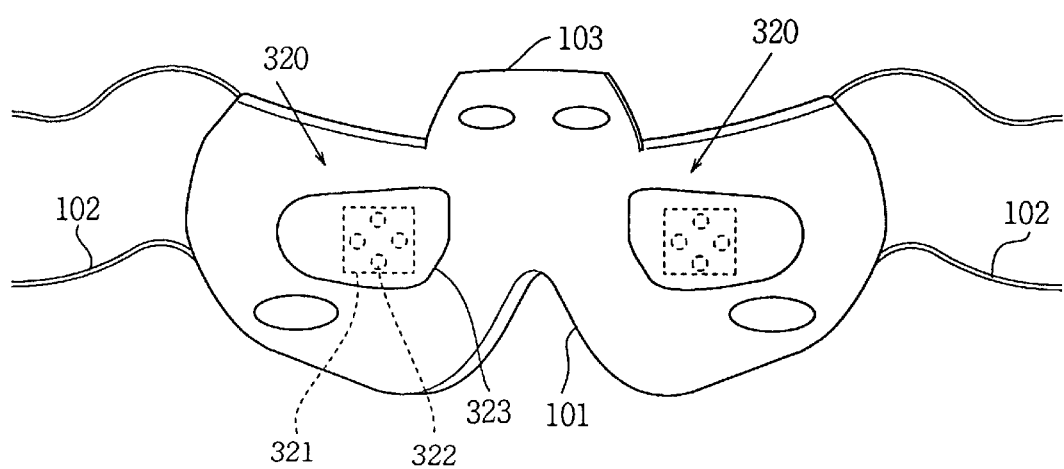

Referring to FIG. 7a, a pair of electrodes 120 and 130 are provided on an inner side of the forehead portion 103 in a lateral direction. A pair of electrodes 140 are provided on opposite lower portions of the bandage 101 at positions corresponding to the cheeks of the face.

Each of these electrodes is formed by, for example a copper foil adhered to the forehead portion 103 and the bandage 101. If the copper foil directly touches the face, the user may feel unpleasant. In order to avoid the unpleasant feeling, a piece of conductive fiber is adhered on each electrode by a conductive adhesive. As the conductive fiber, span polyester fiber with nickel coating is employed.

The electrodes 120 is connected to the GND input of the amplifier 24, namely to the ground through a lead (not shown), the electrode 130 is connected to the minus input, namely the inverted input thereof, and each of the electrodes 140 is connected to the plus input, namely the non-inverted input thereof, respectively.

Since the distance between the plus and minus electrodes is largely set to increase the difference between the input signals, the S/N ratio is improved.

As shown in FIG. 7b, a pair of light emitting members 320 are provided on the inner side of the bandage 101 at positions corresponding to the eyes of the user. Each light emitting member 320 comprises a base portion 321 and LEDs 322 adhered to the base portion 321. A piece of nonwoven fabric 323 is covered on the base portion 321 as a cushion member for avoiding a foreign object feeling. The beams of light emitted from the LEDs 322 of the light emitting members 320 pass through the nonwoven fabric pieces 323 so as to become scattered light and applied to the corresponding eyes of the user for visual stimulation.

Thus, the eye mask device 100 integral with the brain wave sensor and the light emitting element is formed.

Figure 8:
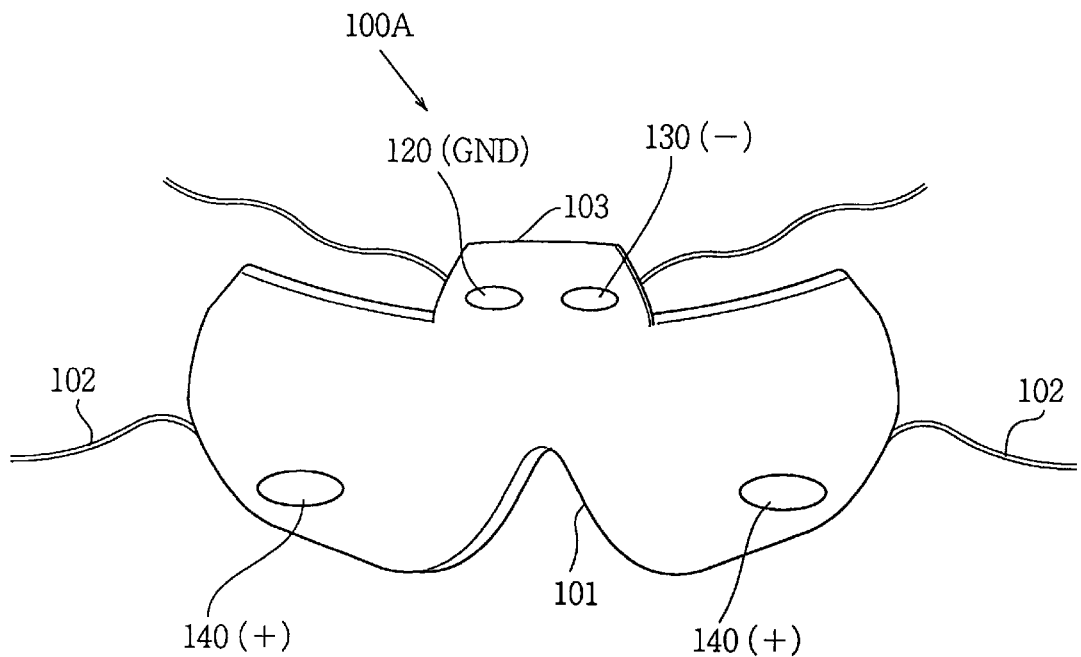
FIG. 8 is a plan view showing a modification of the eye mask.

FIG. 8 shows a modification of the eye mask device. In an eye mask device 100A, one end of each ear strap 102 is connected to a side of the forehead portion 103. Thus, even if the reinforcement member 104 is omitted, the electrodes 120 and 130 can be stably abutted on the forehead by the tensile strength of the rubber straps.

Figure 9:
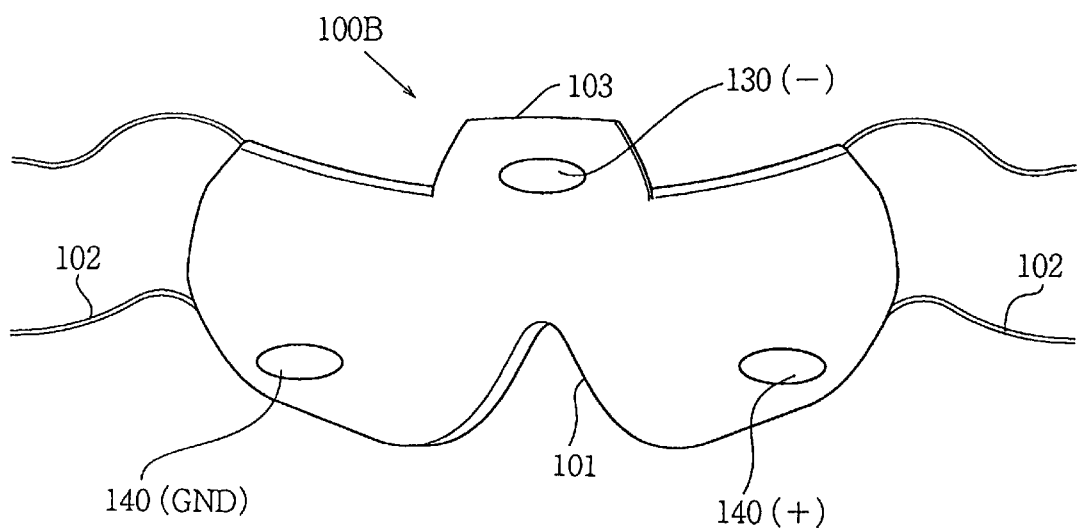
FIG. 9 is a plan view showing another modification of the eye mask.

FIG. 9 shows another modification of the eye mask device. In an eye mask device 100B, the electrode 120 is omitted, and one of the electrodes 140 is connected to the GND input of the amplifier 24 in place of the electrode 120. By such an arrangement, it is possible to detect the brain wave.

(Other embodiments)

Figure 10:
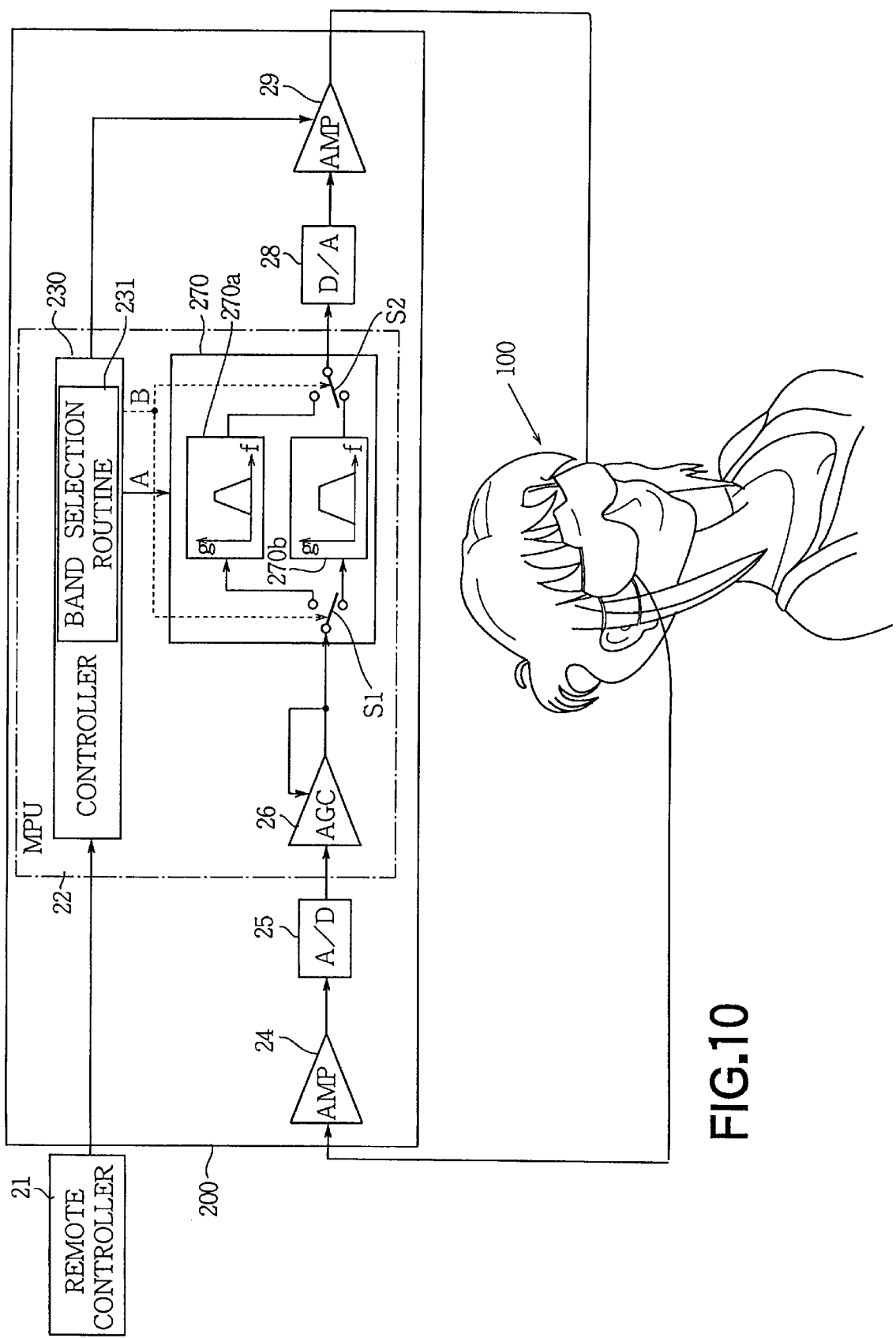
FIG. 10 is a diagram showing a fourth embodiment of the present invention.

FIG. 10 shows a fourth embodiment of the present invention where the eye mask device is employed for the brain wave inducing system of the first embodiment.

Figure 11:
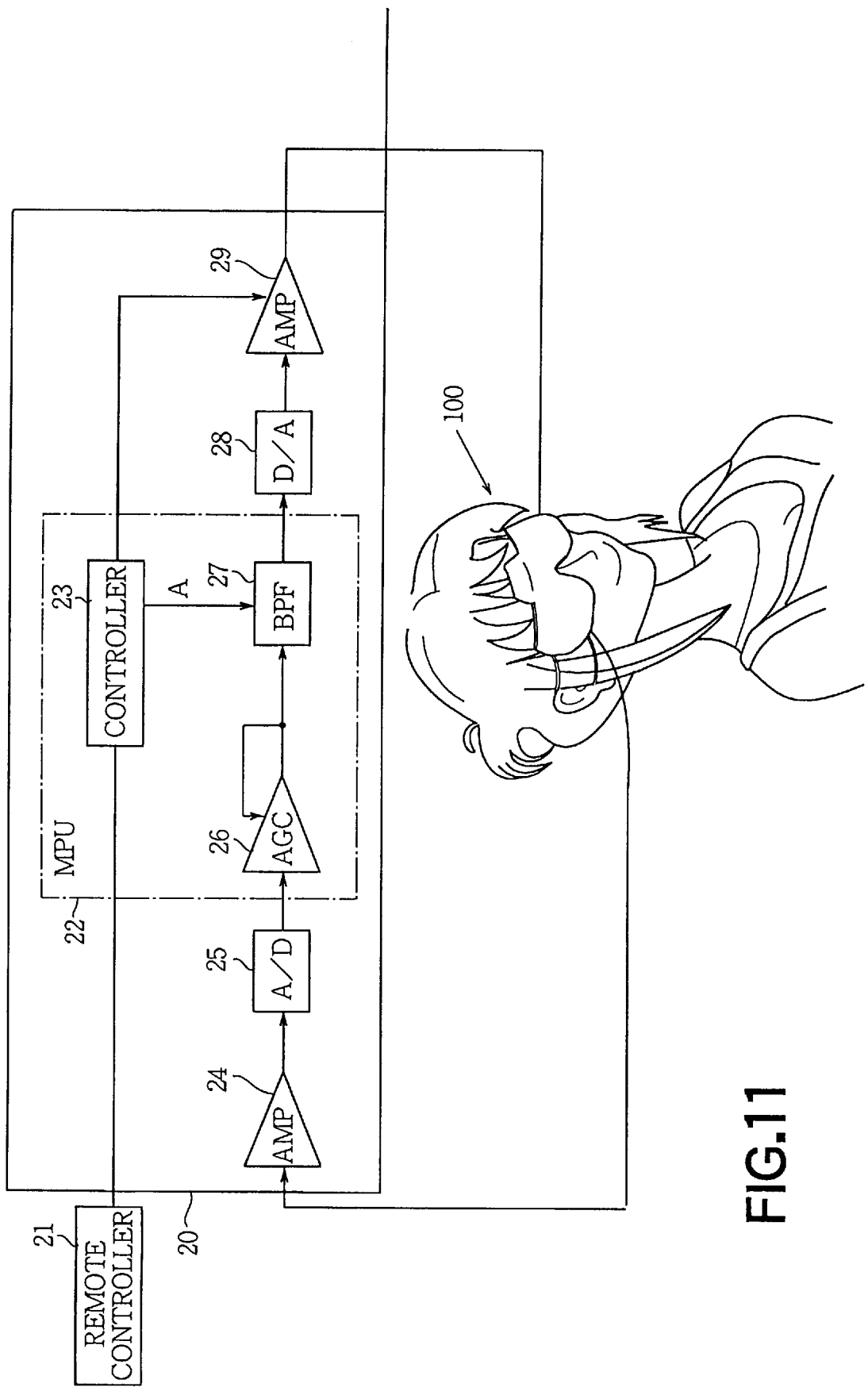
FIG. 11 is a diagram showing a fifth embodiment of the present invention.

FIG. 11 shows a fifth embodiment of the present invention where the eye mask device is employed for the conventional system shown in FIG. 13.

Figure 12:
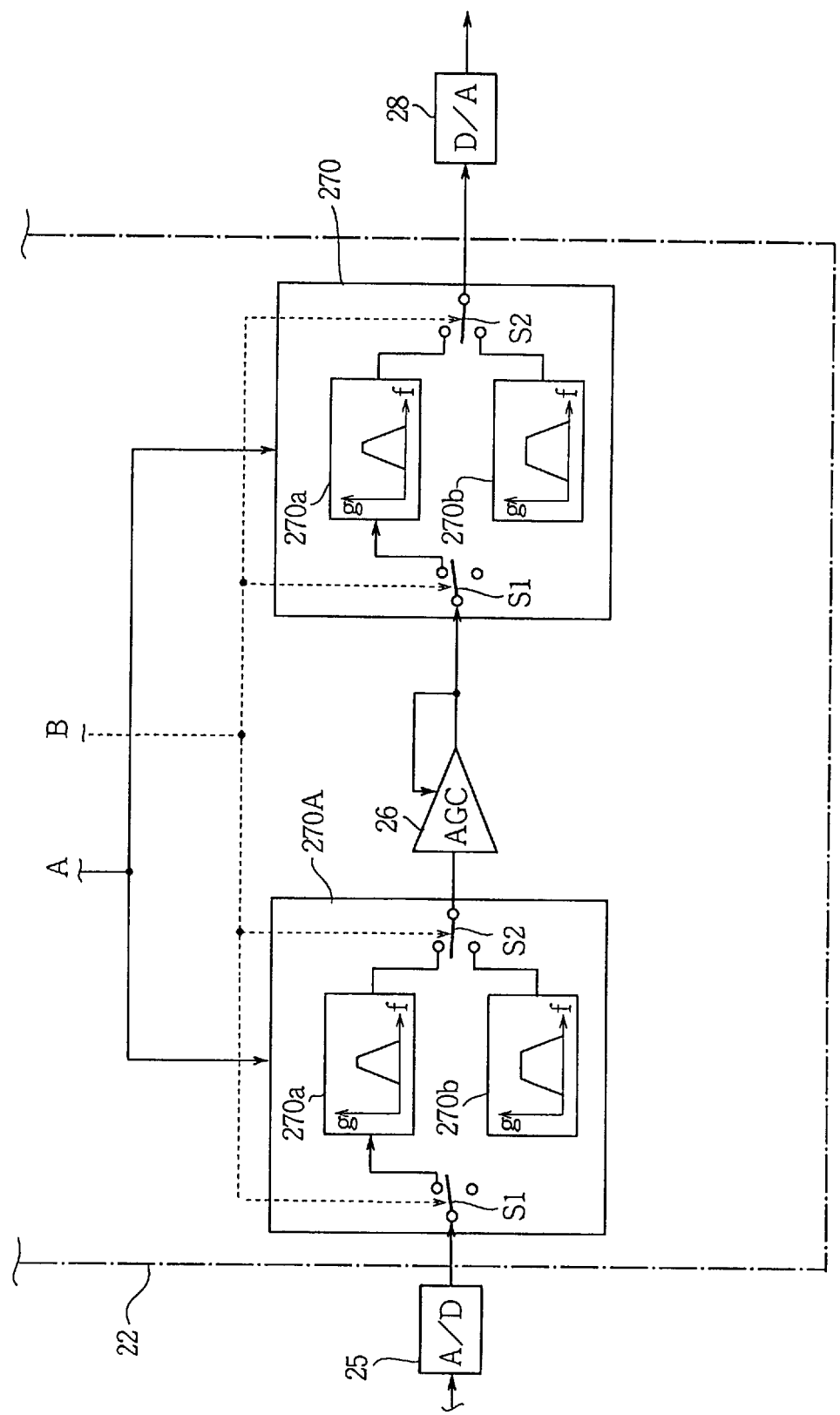
FIG. 12 is a schematic diagram partly showing a modification of the first embodiment.

FIG. 12 shows a modification of the light signal producing system where a BPF unit 270A is provided on a preceding stage of the AGC 26 other than the BPF unit 270 as a following stage.

The characteristics of filters of both BPF units are entirely or approximately the same. Namely, each of the preceding and following BPF units 270A and 270 has the first BPF 270a having the narrow band and the second BPF 270b having the wide band. The pass band of the first BPF of the preceding BPF unit is equal to that of the following BPF unit. Similarly, the pass bands of the second BPFs of the preceding and following BPF units are equal to each other.

In operation, the band of the brain wave is limited by the preceding BPF unit 270A. The gain of the limited signal is controlled by the AGC 26. The following BPF unit 270 operates to remove a distortion in the signal caused by the gain control.

The structure of the system is applicable to the previous embodiments shown in FIGS. 1, 3, 5 and 10.

In order to precisely control the AGC 26 and the BPF units 270A and 270 at a high speed, DSP and a circuit are employed.

In accordance with the present invention, the band for extracting the brain wave is selected by one of the wide and narrow bands. Consequently, it is effective to obtain the sleep inducing effect in addition to the relaxation effect.

The brain wave is stored in the memory in order to reproduce the frequency fluctuation in the sleep transient period. Thus, it is possible to induce the sleep transient state by drawing the brain wave without using the brain wave sensor. Since the troublesome caused by the sensor is avoided, the relaxation effect and sleep inducing effect are further improved.

Since the the brain wave sensor and the light emitting elements are integrally formed in the eye mask device without the ear clip, the relaxation effect can be easily obtained. Furthermore, the relaxation and sleep inducing effects are improved.

While the invention has been described in conjunction with preferred specific embodiment thereof, it will be understood that this description is intended to illustrate and not limit the scope of the invention, which is defined by the following claims.

What is claimed is:

1. A brain wave inducing system comprising:

sensors for detecting brain waves of a user;

a band-pass filter for extracting particular brain waves including an α wave included in a detected brain wave, the band-pass filter comprising a first band-pass filter having a narrow pass band, and a second band-pass filter having a wide pass band connected in parallel to said first band-pass filter;

first selecting means for selecting one of the first and second band-pass filters, wherein said first band pass filter corresponds to an α wave in an eye-closed rest state of the user and has a narrow pass filter corresponding to the α wave in an eye-closed rest state of the user, and wherein said second band pass filter corresponds to an α wave in a sleep transient state of the user and has a wide pass filter corresponding to an α wave in the sleep transient state of the user;

output means for producing a stimulation signal dependent on an α wave extracted by a selected band-pass filter; and light emitting means responsive to the stimulation signal for emitting a stimulation light to the user.

2. The system according to claim 1 further comprising a memory for recording the extracted brain waves and for reproducing the recorded brain waves, and second selecting means for selecting either of the recording or reproducing of the brain waves.

3. The system according to claim 1 wherein the sensors are mounted on an eye mask to be attached to a forehead of the user.

4. The system according to claim 2 further comprising detecting means for detecting a sleep falling point when the user falls into sleep and producing a signal, the second selecting means being provided to select the recording of the brain waves from the starting of the extraction of the brain waves to until receiving the signal of the sleep falling point.

5. The system according to claim 4 wherein the detecting means detects the sleep falling point by detecting a time when α wave appearance rate reduces 50% from a reference value.

6. The system according to claim 3 wherein the eye mask has a resilient member so as to be curved along the forehead.

* * * * *